(12) United States Patent
Hsiung (10) Patent No.: US 9,765,928 B2
(45) Date of Patent: Sep. 19, 2017

(54) PRESSURE REGULATING OXYGEN BOTTLE

(71) Applicant: BESMED HEALTH BUSINESS CORP., New Taipei (TW)

(72) Inventor: Tao-Tsun Hsiung, New Taipei (TW)

(73) Assignee: NINGBO BESMED MEDICAL EQUIPMENT CORP., Zhejiang (CN)

( * ) Notice: Subject to any disclaimer, the term of this patent is extended or adjusted under 35 U.S.C. 154(b) by 722 days.

(21) Appl. No.: 14/316,004

(22) Filed: Jun. 26, 2014

(65) Prior Publication Data

US 2015/0292676 A1 Oct. 15, 2015

(30) Foreign Application Priority Data

Apr. 15, 2014 (TW) .............................. 103206500 U (51) Int. Cl.
*A61M 16/20* (2006.01)
*F17C 1/00* (2006.01)
*A61M 16/00* (2006.01)

(52) U.S. Cl.
CPC .............. *F17C 1/00* (2013.01); *A61M 16/00* (2013.01); *A61M 16/201* (2014.02); *A61M 2205/3348* (2013.01); *A61M 2240/00* (2013.01); *F17C 2205/0192* (2013.01); *F17C 2227/0121* (2013.01); *F17C 2270/025* (2013.01)

(58) Field of Classification Search
CPC .............. A61M 16/00; A61M 16/0003; A61M 16/0057; A61M 16/201; F17C 1/00; B65D 51/16; B65D 51/1611; B65D 51/1616; B65D 51/1644; B65D 51/1661

USPC ......... 141/63, 64; 220/371, 373, 374, 367.1; 215/307, 308, 311; 206/459.1
See application file for complete search history.

(56) References Cited

U.S. PATENT DOCUMENTS

| | | | | |
|---|---|---|---|---|
| 3,710,780 A | * | 1/1973 | Milch | A63B 23/18 482/13 |
| 3,869,771 A | * | 3/1975 | Bollinger | A61M 16/01 128/200.13 |
| 6,988,497 B2 | * | 1/2006 | Levine | A61M 16/167 128/203.17 |
| 7,077,154 B2 | * | 7/2006 | Jacobs | A61M 16/0666 128/201.23 |
| 7,228,859 B2 | * | 6/2007 | Loescher | A61M 16/16 128/203.12 |

(Continued)

*Primary Examiner* — Justine Yu
*Assistant Examiner* — Kathrynn Lyddane
(74) *Attorney, Agent, or Firm* — WPAT, P.C., Intellectual Property Attorneys; Anthony King (57) ABSTRACT

A pressure regulating oxygen bottle has a bottle body filled with liquid, a cap mounted on the bottle body, an outer tube mounted in the bottle body, and an inner tube mounted through the cap and protruding in the outer tube. The outer tube has multiple flow holes arranged linearly between two opposite ends of the outer tube. The inner tube is connected to an artificial respiration system and has multiple communicating holes arranged spirally between two opposite ends of the inner tube. By turning the inner tube to allow one of the communicating holes to align with a corresponding one of the flow holes of the outer tube, a hydrostatic pressure formed between a liquid surface of the liquid and the communicating hole is changed. Accordingly, gas pressure inside the artificial respiration system can be adjusted.

18 Claims, 6 Drawing Sheets

(56) References Cited

U.S. PATENT DOCUMENTS

| | | | |
|---|---|---|---|
| 8,235,042 B2 * | 8/2012 | Newman, Jr. | A61M 16/0666 128/200.24 |
| 2012/0160242 A1 * | 6/2012 | Gutierrez Fonseca | A61M 16/00 128/203.26 |
| 2015/0258291 A1 * | 9/2015 | Richards-Kortum | A61M 16/12 128/201.22 |

* cited by examiner

PRESSURE REGULATING OXYGEN BOTTLE

BACKGROUND OF THE INVENTION

1. Field of the Invention

The present invention relates to an oxygen bottle, especially to a pressure regulating oxygen bottle that is connected to an artificial respiration system and regulates a gas pressure of gas discharging from the oxygen bottle so as to control the gas pressure inside the artificial respiration system.

2. Description of the Prior Art(s)

An artificial respiration system is usually used for assisting preterm infants or newborn infants to breathe. A gas pressure of an airflow flowing in the artificial respiration system is higher than an atmospheric pressure outside the artificial respiration system. The airflow delivers oxygen to the infant via an oxygen mask that covers nose and mouth of the infant or via a nasal cannula. The gas pressure in the artificial respiration system is formed by a resistant force applied to an end of a pipe line of the artificial respiration system.

Conventionally, the end of the pipe line of the artificial respiration system is mounted into a bottle filled with liquid. A difference in height between a liquid surface of the liquid and the end of the pipe line forms a hydrostatic pressure. The hydrostatic pressure hinders the gas of the artificial respiration system from discharging. Thus, the gas pressure inside the artificial respiration system is increased to higher than the atmospheric pressure outside the artificial respiration system.

An air pressure gauge may be connected to the artificial respiration system to monitor the gas pressure inside the artificial respiration system. Otherwise, multiple marks marking depths in the bottle may be formed on a sidewall of the bottle. Thus, by observing depths of the end of the pipe line of the artificial respiration system that protrudes in the bottle, the gas pressure inside the artificial respiration system can be calculated.

However, since it is hard to control the depths of the end of the pipe line of the artificial respiration system in the bottle, the gas pressure of the artificial respiration system cannot be adjusted quickly and precisely according to user's need. Moreover, the bottle cannot hold the end of the pipe line at specific depths. Therefore, adjusting the depth of the end of the pipe line to form a stable gas pressure in the artificial respiration system is inconvenient and troublesome to the users.

To overcome the shortcomings, the present invention provides a pressure regulating oxygen bottle to mitigate or obviate the aforementioned problems.

SUMMARY OF THE INVENTION

The main objective of the present invention is to provide a pressure regulating oxygen bottle. The pressure regulating oxygen bottle has a bottle body, a cap mounted on the bottle body, an outer tube mounted in the bottle body, and an inner tube mounted through the cap and protruding in the outer tube. The bottle body is filled with liquid. The outer tube has multiple flow holes arranged linearly between two opposite ends of the outer tube. The inner tube is connected to an artificial respiration system and has multiple communicating holes arranged spirally between two opposite ends of the inner tube.

By turning the inner tube to allow one of the communicating holes to align with a corresponding one of the flow holes of the outer tube, a hydrostatic pressure formed between a liquid surface of the liquid and the communicating hole is changed. Accordingly, gas pressure inside the artificial respiration system can be adjusted.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
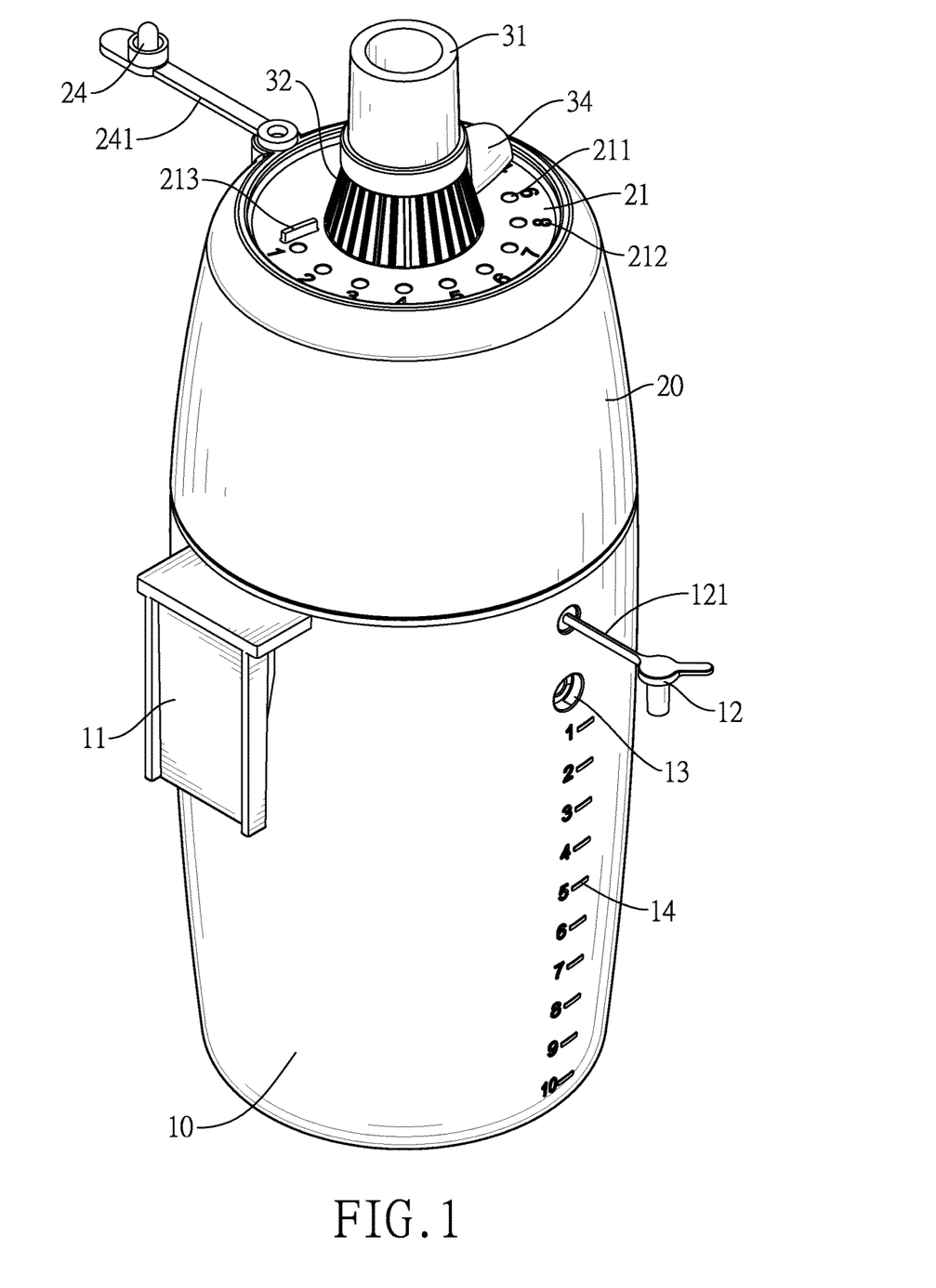
FIG. 1 is a perspective view of a first embodiment of a pressure regulating oxygen bottle in accordance with the present invention.
Figure 2:
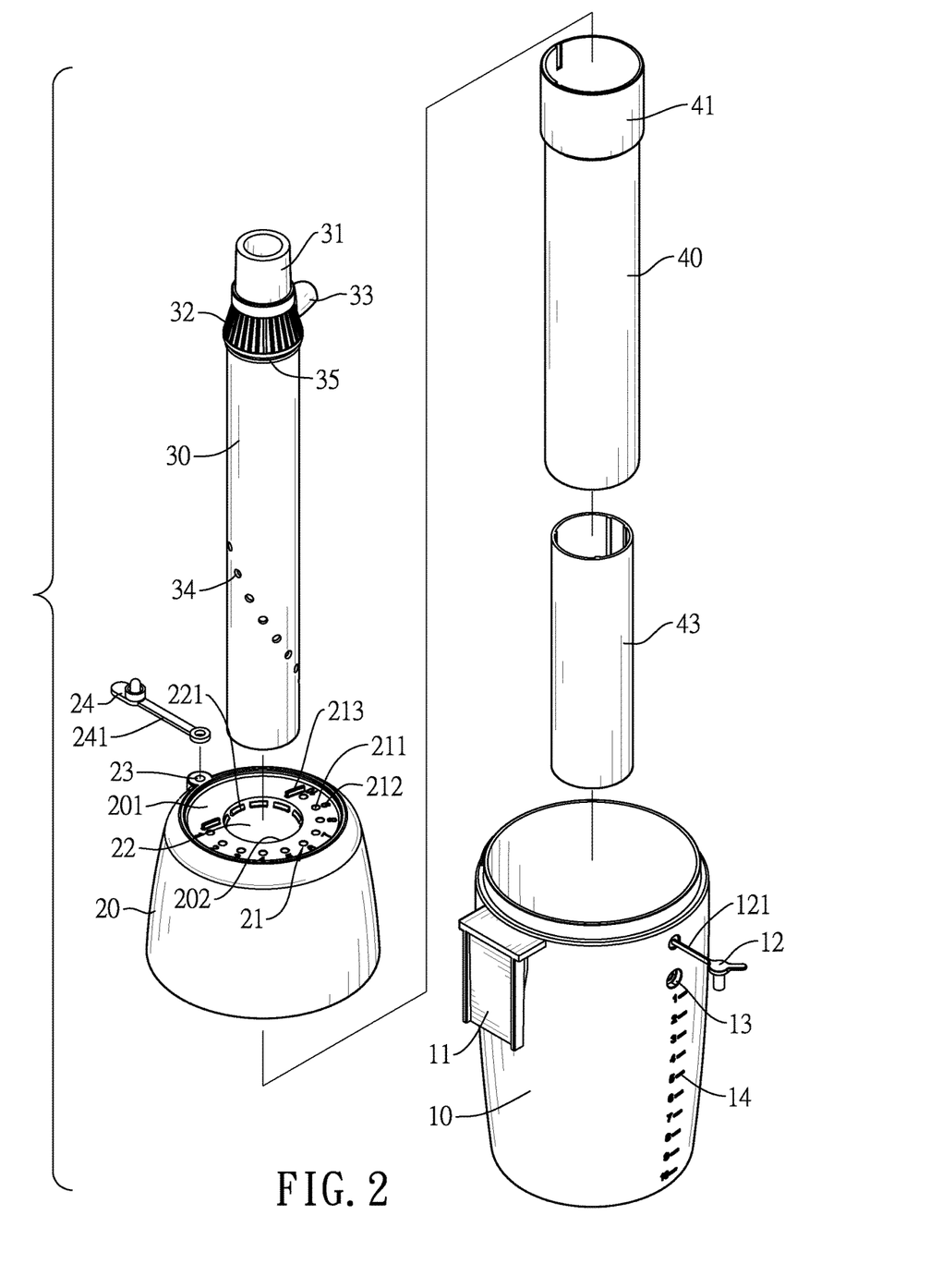
FIG. 2 is an exploded perspective view of the pressure regulating oxygen bottle in FIG. 1.

With reference to FIGS. 1 and 2, a pressure regulating oxygen bottle in accordance with the present invention comprises a bottle body 10, a cap 20, an outer tube 40, and an inner tube 30.

Figure 3:
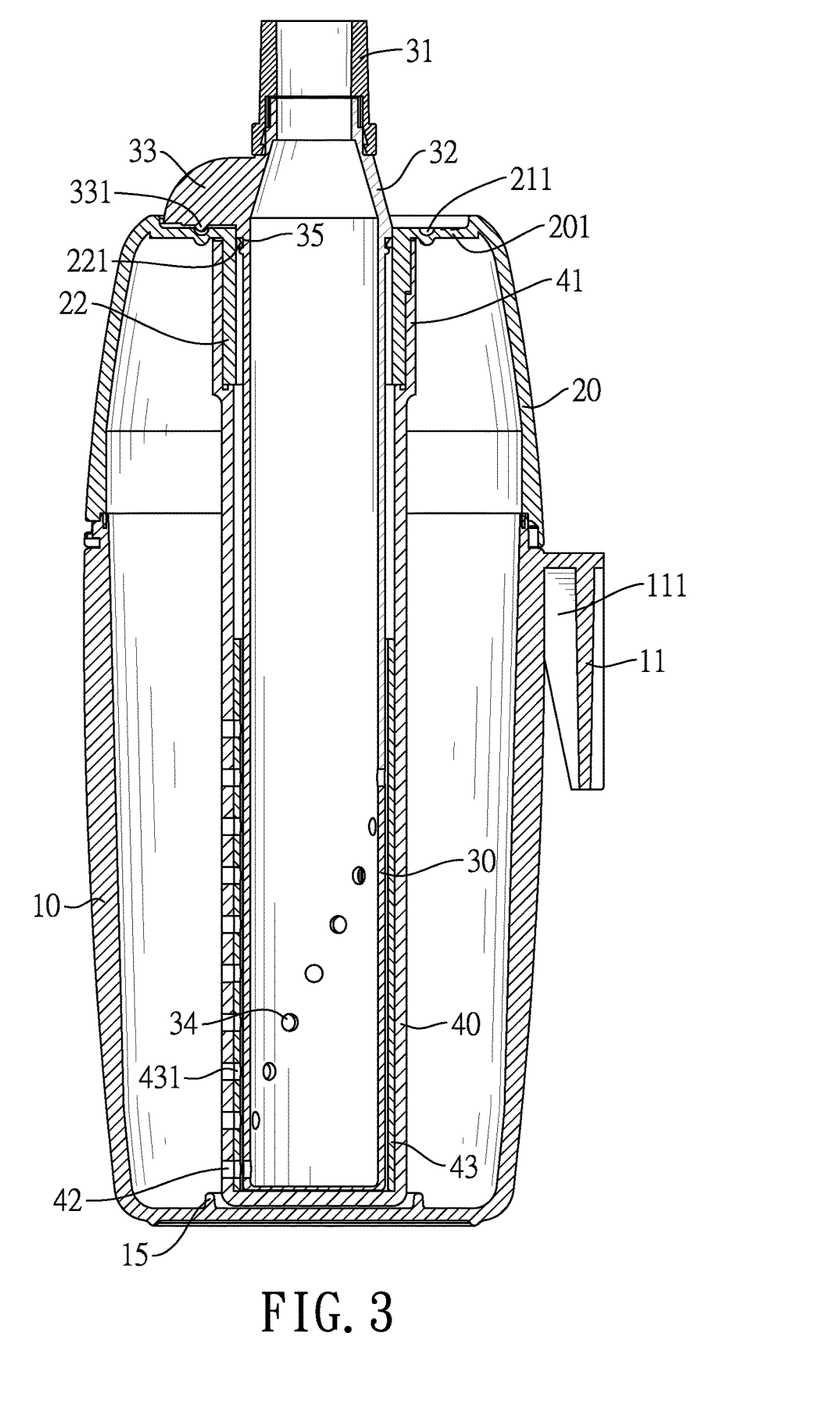
FIG. 3 is a cross-sectional side view of the pressure regulating oxygen bottle in FIG. 1.

With further reference to FIG. 3, the bottle body 10 has an open end, a closed end, a sidewall, a mount 11, a through hole 13, a hole plug 12, multiple marks 14, and a mounting seat 15.

The closed end of the bottle body 10 has an inner end surface. The sidewall of the bottle body 10 has an outer side surface. The mount 11 is disposed adjacent to the open end of the bottle body 10 and is attached to the outer side surface of the side wall of the bottle body 10 via a connecting wing 111. A width of the connecting wing 111 decreases from the open end of the bottle body 10 toward the closed end of the bottle body 10.

The through hole 13 of the bottle body 10 is formed through the sidewall of the bottle body 10 and communicates with an interior of the bottle body 10. The hole plug 12 of the bottle body 10 is detachably plugged in the through hole 13 of the bottle body 10 to selectively seal the through hole 13 of the bottle body 10, and is connected to the sidewall of the bottle body 10 via an extending strip 121.

The marks 14 are formed on the outer surface of the bottle body 10, are arranged linearly between the open end of the bottle body 10 and the closed end of the bottle body 10, and are separated by a same distance. The mounting seat 15 is formed on the inner end surface of the closed end of the bottle body 10. Specifically, the mounting seat 15 is an annular protrusion.

When setting up an artificial respiration system, the mount 11 is used for hanging the pressure regulating oxygen bottle on a specific place. Gas or excessive liquid inside the bottle body 10 can be discharged from the through hole 13 of the bottle body 10. Moreover, a user can see an amount of the liquid inside the bottle body 10 through the marks 14.

The cap 20 is mounted on the open end of the bottle body 10 and has an open end, an end panel 201, an outer side surface, an indication portion 21, a connection portion 22, multiple engaging protrusions 221, a through hole 23, and a hole plug 24.

The open end of the cap 20 is mounted on the open end of the bottle body 10. The end panel 201 is formed opposite to the open end of the cap 20 and has an outer end surface, an inner end surface, and a mounting hole 202.

The mounting hole 202 is formed through the end panel 201 and is disposed at a center of the end panel 201.

The indication portion 21 is formed on the outer end surface of the end panel 201 of the cap 20. In the preferred embodiment, the indication portion 21 has two stops 213, multiple positioning holes 211, and multiple labels 212. The stops 213 are separately formed on the outer end surface of the end panel 201. The positioning holes 211 are formed on the outer end surface of the end panel 201, are arranged in an arc between the stops 213, and are separated by a same distance. The labels 212 are formed on the outer end surface of the end panel 201 and respectively correspond in position to the positioning holes 211.

The connection portion 22 is tubular, is formed on the inner end surface of the end panel 201, is mounted around the mounting hole 202 of the end panel 201, protrudes toward the open end of the cap 20, and is mounted between the outer tube 40 and the inner tube 30. The connection portion 22 has an inner surface and an outer surface. The engaging protrusions 221 are separately formed on and arranged around the inner surface of the connection portion 22.

The through hole 23 of the cap 20 is formed through the cap 20 and communicates with an interior of the cap 20. The hole plug 24 of the cap 20 is detachably plugged in the through hole 23 of the cap 20 to selectively seal the through hole 23 of the cap 20, and is connected to the outer side surface of the cap 20 via an extending strip 241.

The outer tube 40 is mounted in the bottle body 10 and has a sidewall, a closed end, an open end 41, multiple flow holes 42, and a covering 43.

The sidewall of the outer tube 40 has an inner surface. The closed end of the outer tube 40 is mounted in the mounting seat 15 of the bottle body 10. The open end 41 of the outer tube 40 is attached to the end panel 201 of the cap 20 and is mounted around the outer surface of the connection portion 22 of the cap 20. A diameter of the open end 41 of the outer tube 40 is larger than a diameter of the closed end of the outer tube 40.

The flow holes 42 are separately formed through the sidewall of the outer tube 40, are arranged linearly between the closed end of the outer tube 40 and the open end 41 of the outer tube 40, and are separated by a same distance.

The covering 43 is tubular, is attached to the inner surface of the sidewall of the outer tube 40, is disposed adjacent to the closed end of the outer tube 40, and has multiple intermediate holes 431. The intermediate holes 431 are separately formed through the covering 43, are linearly arranged, are separated by a same distance, and respectively align with the flow holes 42 of the outer tube 40. In the preferred embodiment, the covering 43 is a silicone layer adhered to the inner surface of the outer tube 40.

The inner tube 30 is rotatably mounted through the mounting hole 202 of the end panel 201 of the cap 20 and the connection portion 22 of the cap 20, is connected to the cap 20, is rotatably mounted in the outer tube 40, and abuts the covering 43. The inner tube 30 has a sidewall, a closed end, an open end, a connecting pipe 31, an adjusting portion 32, an engaging groove 35, an indicator 33, and multiple communicating holes 34.

The sidewall of the inner tube 30 has an outer surface. The closed end of the inner tube 30 protrudes in and abuts the covering 43 of the outer tube 40. The open end of the inner tube 30 protrudes out from the cap 20 and is tapered. The connecting pipe 31 is mounted on the open end of the inner tube 30. The adjusting portion 32 is formed on the outer surface of the sidewall of the inner tube 30 and around the open end of the inner tube 30, and is tapered. The adjusting portion 32 has a lower edge. The engaging groove 35 is formed in and around the outer surface of the sidewall of the inner tube 30, is disposed adjacent to the open end of the inner tube 30, and engages with the engaging protrusions 221 of the cap 20. Specifically, the engaging groove 35 is formed in and around the lower edge of the adjusting portion 32 of the inner tube 30.

The indicator 33 is formed on and protrudes from the adjusting portion 32 and has a bottom and a positioning protrusion 331. The bottom of the indicator 33 faces the indication portion 21 of the cap 20. The positioning protrusion 331 is formed on the bottom of the indicator 33 and selectively engages in one of the positioning holes 211 of the indication portion 21 of the cap 20.

The communicating holes 34 are separately formed through the sidewall of the inner tube 30, are arranged spirally between the closed end of the inner tube 30 and the open end of the inner tube 30, and are separated by a same distance. Each communicating hole 34 selectively aligns with a corresponding one of the intermediate holes 431 of the covering 43 of the outer tube 40 and a corresponding one of the flow holes 42 of the outer tube 40.

When the inner tube 30 is turned, the indicator 33 corresponds in position to one of the labels 212 of the indication portion 21. A turning range of the inner tube 30 is limited between the stops 213 of the indication portion 21. When the positioning protrusion 331 of the indicator 33 of the inner tube 30 engages in one of the positioning holes 211 of the indication portion 21 of the cap 20, one of the communicating holes 34 of the inner tube 30 aligns with the corresponding intermediate hole 431 of the covering 43 and the corresponding flow hole 42 of the outer tube 40.

As shown in FIGS. 2 and 3, in the preferred embodiment, the indication portion 21 of the cap 20 has ten positioning holes 211 and ten labels 212. The ten positioning holes 211 are formed on the outer end surface of the end panel 201 of the cap 20 and are arranged in an arc between the stops 213. The labels 212 respectively label the positioning holes 211 with Arabic numeral 1 to 10. The outer tube 40 has ten flow holes 42 arranged linearly between the closed end 41 of the outer tube 40 and the open end of the outer tube 40 and separated by the same distance. Accordingly, the covering 43 of the outer tube 40 also has ten intermediate holes 431 linearly arranged and separated by the same distance. The inner tube 30 has ten communicating holes 34 arranged spirally between the closed end of the inner tube 30 and the open end of the inner tube 30 and separated by the same distance.

Figure 6:
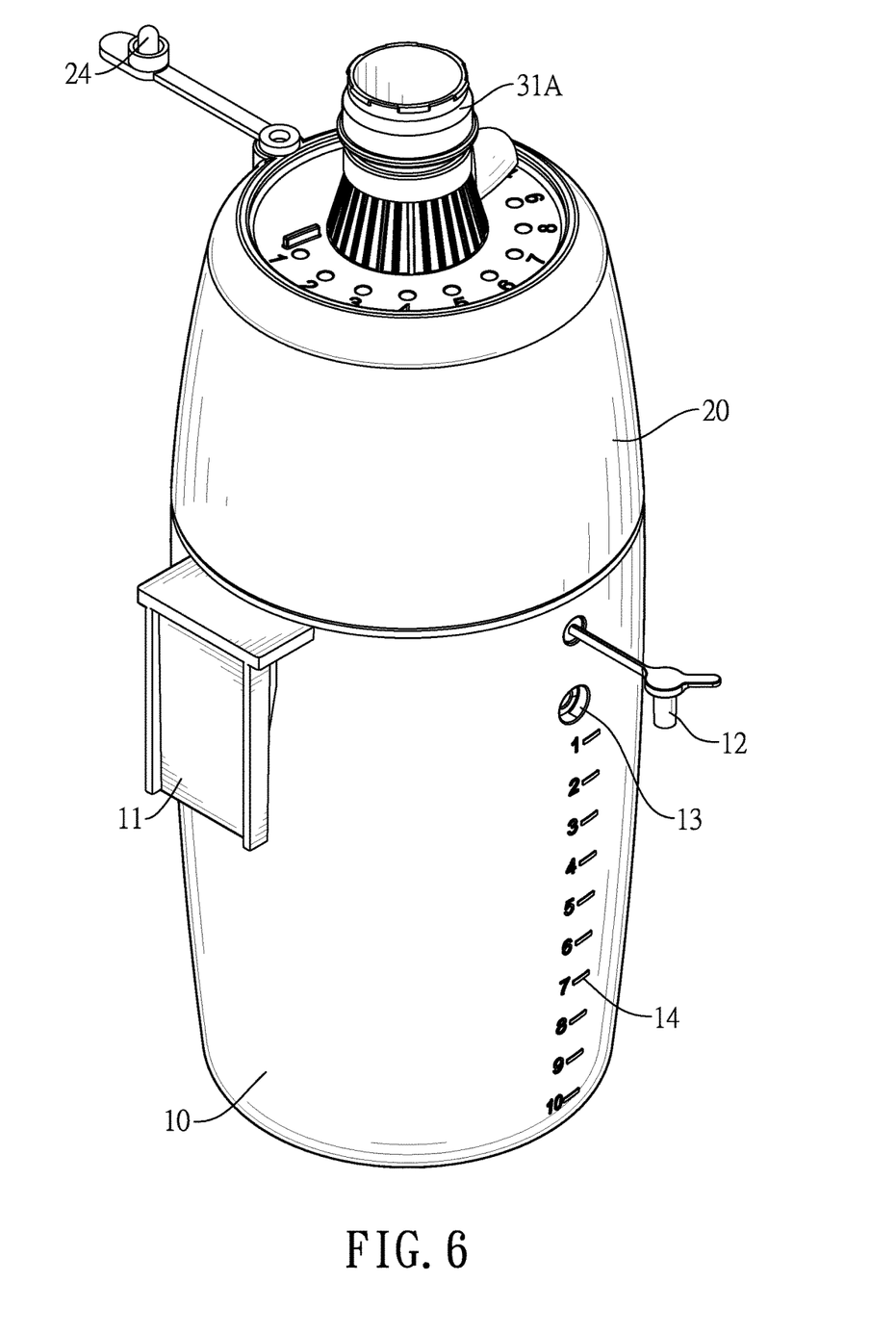
FIG. 6 is a perspective view of a second embodiment of a pressure regulating oxygen bottle in accordance with the present invention.

With further reference to FIG. 6, in another preferred embodiment, the connecting pipe 31A further has an annular protrusion formed around an outer surface of the connecting pipe 31A. The connecting pipe 31, 31A can be replaced with different types of the connecting pipes 31, 31A so as to connect with the artificial respiration system having different types of connectors.

Figure 4:
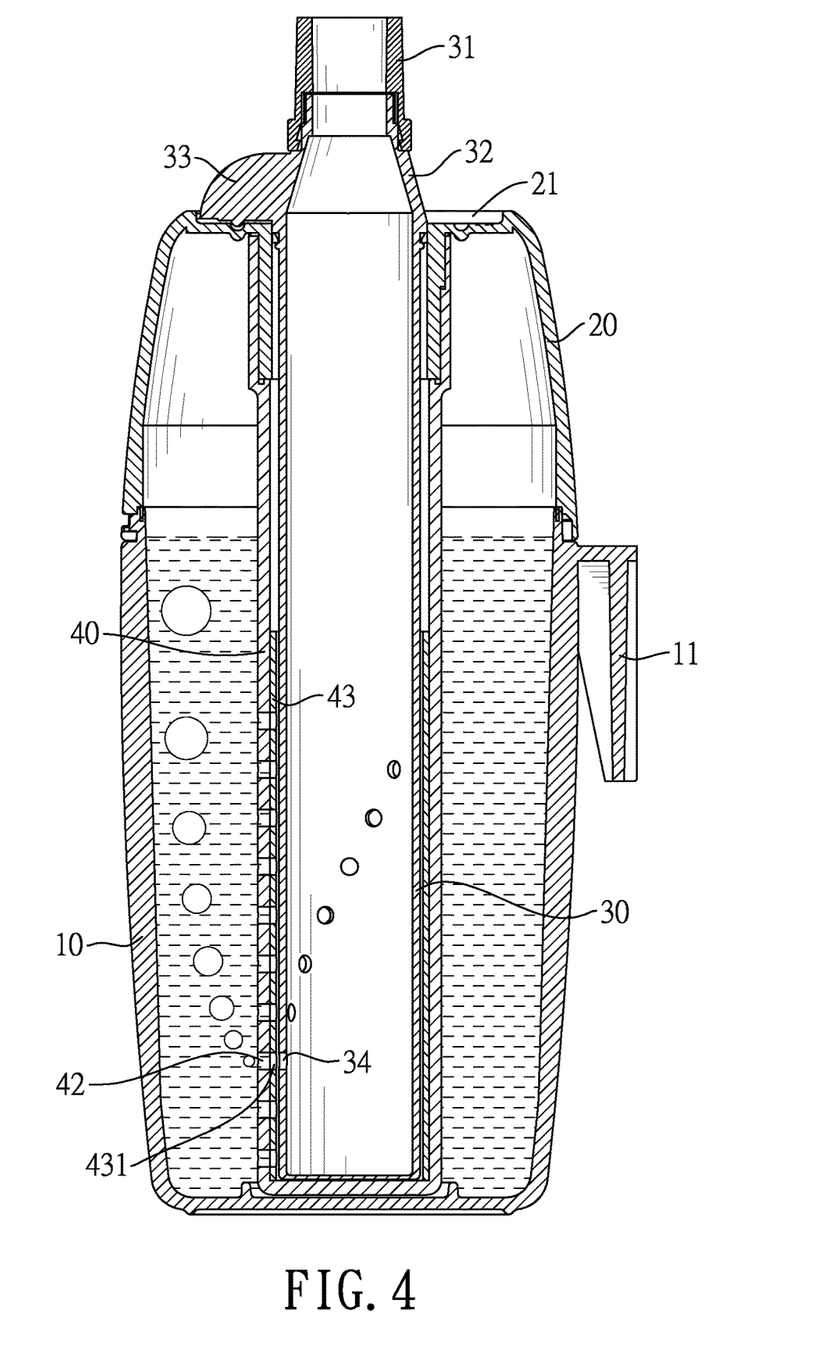
FIG. 4 is an operational cross-sectional side view of the pressure regulating oxygen bottle in FIG. 1.

With further reference to FIG. 4, when the pressure regulating oxygen bottle of the present invention is in use, the connecting pipe 31 of the inner tube 30 is connected to the artificial respiration system, the interior of the bottle body 10 is filled with liquid, and the liquid does not flow into the outer tube 40 and the inner tube 30. Gas inside the artificial respiration system tends to discharge from the pressure regulating oxygen bottle.

The user holds the adjusting portion 32 of the inner tube 30 to turn the inner tube 30 to allow one of the communicating holes 34 of the inner tube 30 to align with the corresponding intermediate hole 431 of the covering 43 and the corresponding flow hole 42 of the outer tube 40. A hydrostatic pressure is formed by a height difference between a liquid surface of the liquid and the communicating hole 34. The hydrostatic pressure hinders the gas of the artificial respiration system from discharging from the communicating hole 34 of the inner tube 30, the intermediate hole 431 of the covering 43, and the flow hole 42 of the outer tube 40. Accordingly, gas pressure inside the artificial respiration system is increased to higher than an atmospheric pressure outside the artificial respiration system.

The gas from the artificial respiration system forms bubbles to pass through the liquid in the bottle body 10 and the bubbles burst at the liquid surface of the liquid. Then the gas discharges from the through holes 13, 23 of the bottle body 10 and the cap 20. Moreover, with the covering 43 filling space formed between the inner tube 30 and the outer tube 40, the gas from the artificial respiration system does not flow into and discharges from the space between the inner tube 30 and the outer tube 40.

As shown in FIG. 4, as the inner tube 30 is turned to allow the communicating hole 34 that is disposed adjacent to the closed end of the inner tube 30 to align with a corresponding one of the intermediate holes 431 and a corresponding one of the flow holes 42, a higher hydrostatic pressure is formed. Accordingly, the gas pressure inside the artificial respiration system is increased.

Figure 5:
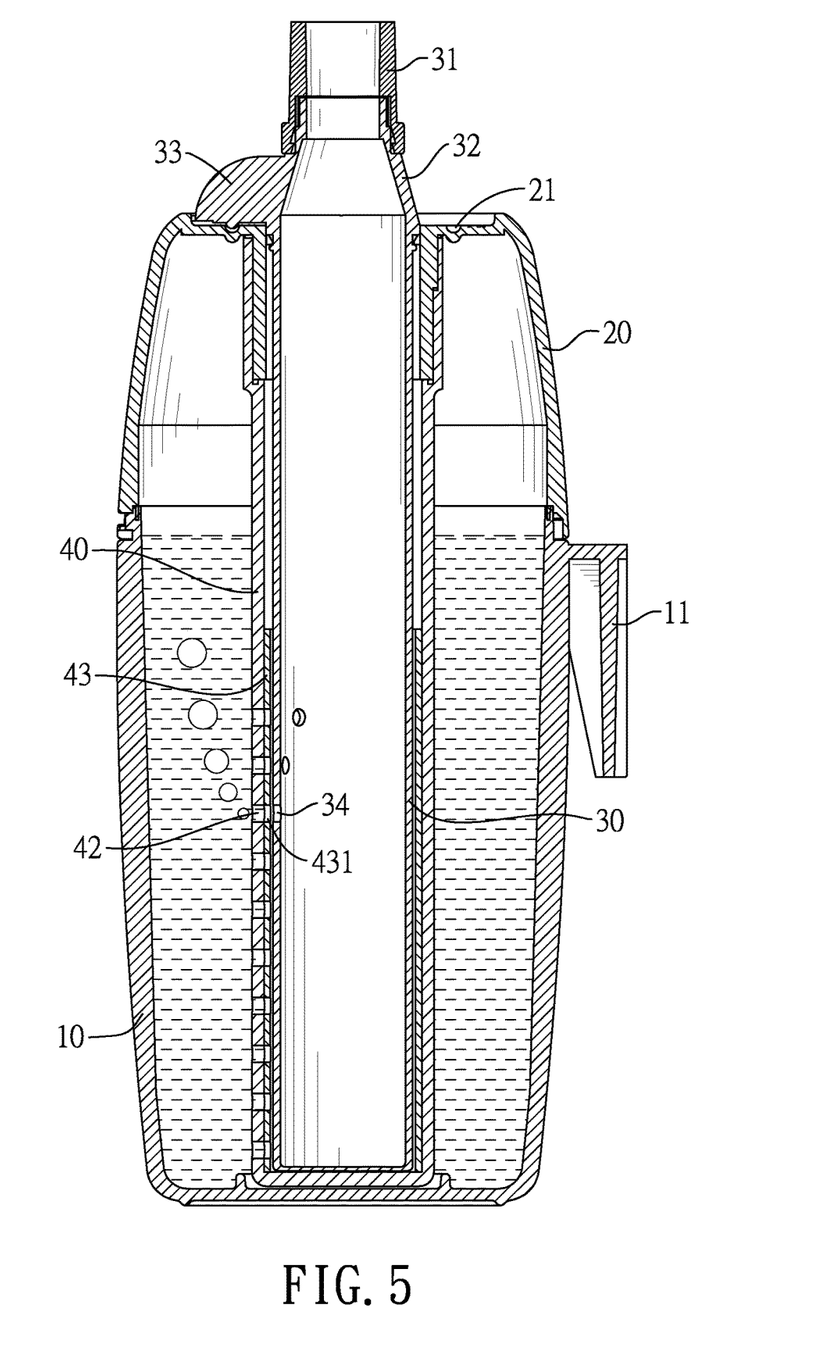
FIG. 5 is another operational cross-sectional side view of the pressure regulating oxygen bottle in FIG. 1.

With further reference to FIG. 5, as the inner tube 30 is turned to allow the communicating hole 34 that is disposed adjacent to the open end of the inner tube 30 to align with a corresponding one of the intermediate holes 431 and a corresponding one of the flow holes 42, a lower hydrostatic pressure is formed. Accordingly, the gas pressure inside the artificial respiration system is lowered.

The pressure regulating oxygen bottle as described has the following advantages. By turning the inner tube 30 to allow one of the communicating holes 34 to align with the corresponding intermediate hole 431 of the covering 43 and the corresponding flow hole 42 of the outer tube 40, the hydrostatic pressure formed between the liquid surface of the liquid and the communicating hole 34 can be changed. Accordingly, the gas pressure inside the artificial respiration system can be adjusted easily.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A pressure regulating oxygen bottle comprising:
a bottle body having an open end and a closed end;
a cap mounted on the open end of the bottle body and having
an open end mounted on the open end of the bottle body; and
an end panel formed opposite to the open end of the cap and having a mounting hole;
an outer tube mounted in the bottle body and having
a sidewall;
a closed end;
an open end attached to the end panel of the cap; and
multiple flow holes separately formed through the sidewall of the outer tube, and arranged linearly between the closed end of the outer tube and the open end of the outer tube; and
an inner tube rotatably mounted through the mounting hole of the end panel of the cap, connected to the cap, and having
a sidewall;
a closed end protruding in the outer tube;
an open end protruding out from the cap; and
multiple communicating holes separately formed through the sidewall of the inner tube and arranged spirally between the closed end of the inner tube and the open end of the inner tube, and each communicating hole selectively aligning with a corresponding one of the flow holes of the outer tube.

2. The pressure regulating oxygen bottle as claimed in claim 1, wherein
the closed end of the bottle body has an inner end surface;
the bottle body further has
a sidewall having an outer side surface;
a mount disposed adjacent to the open end of the bottle body and attached to the outer side surface of the sidewall of the bottle body;
a through hole formed through the sidewall of the bottle body and communicating with an interior of the bottle body;
a hole plug detachably plugged in the through hole of the bottle body and connected to the sidewall of the bottle body via an extending strip;
multiple marks formed on an outer surface of the bottle body, and arranged linearly between the open end of the bottle body and the closed end of the bottle body; and
a mounting seat formed on the inner end surface of the closed end of the bottle body; and
the closed end of the outer tube is mounted in the mounting seat of the bottle body.

3. The pressure regulating oxygen bottle as claimed in claim 1, wherein
the end panel of the cap further has an outer end surface and an inner end surface;
the cap further has
an indication portion formed on the outer end surface of the end panel of the cap;
a connection portion being tubular, formed on the inner end surface of the end panel, mounted around the mounting hole of the end panel, protruding toward the open end of the cap, and mounted between the outer tube and the inner tube;
a through hole formed through the cap; and
a hole plug detachably plugged in the through hole of the cap and connected to an outer side surface of the cap via an extending strip.

4. The pressure regulating oxygen bottle as claimed in claim 2, wherein the end panel of the cap further has an outer end surface and an inner end surface;

the cap further has
an indication portion formed on the outer end surface of the end panel of the cap;
a connection portion being tubular, formed on the inner end surface of the end panel, mounted around the mounting hole of the end panel, protruding toward the open end of the cap, and mounted between the outer tube and the inner tube;
a through hole formed through the cap; and
a hole plug detachably plugged in the through hole of the cap and connected to an outer side surface of the cap via an extending strip.

5. The pressure regulating oxygen bottle as claimed in claim 3, wherein
the connection portion of the cap has an inner surface;
the cap further has multiple engaging protrusions separately formed on and arranged around the inner surface of the connection portion of the cap;
the sidewall of the inner tube has an outer surface; and
the inner tube further has an engaging groove formed in and around the outer surface of the sidewall of the inner tube, disposed adjacent to the open end of the inner tube and engaging with the engaging protrusions of the cap.

6. The pressure regulating oxygen bottle as claimed in claim 4, wherein
the connection portion of the cap has an inner surface;
the cap further has multiple engaging protrusions separately formed on and arranged around the inner surface of the connection portion of the cap;
the sidewall of the inner tube has an outer surface; and
the inner tube further has an engaging groove formed in and around the outer surface of the sidewall of the inner tube, disposed adjacent to the open end of the inner tube and engaging with the engaging protrusions of the cap.

7. The pressure regulating oxygen bottle as claimed in claim 3, wherein
the indication portion of the cap has
two stops separately formed on the outer end surface of the end panel;
multiple positioning holes formed on the outer end surface of the end panel and arranged in an arc between the stops; and
multiple labels formed on the outer end surface of the end panel and respectively corresponding in position to the positioning holes;
the inner tube further has
a connecting pipe mounted on the open end of the inner tube;
an adjusting portion formed on the outer surface of the sidewall of the inner tube and around the open end of the inner tube, and the adjusting portion having a lower edge; and
an indicator formed on and protruding from the adjusting portion and having
a bottom facing the indication portion of the cap; and
a positioning protrusion formed on the bottom of the indicator and selectively engaging in one of the positioning holes of the indication portion of the cap; and
the engaging groove of the inner tube is formed in and around the lower edge of the adjusting portion of the inner tube;
wherein when the positioning protrusion of the indicator of the inner tube engages in one of the positioning holes of the indication portion of the cap, one of the communicating holes of the inner tube aligns with the corresponding flow hole of the outer tube.

8. The pressure regulating oxygen bottle as claimed in claim 4, wherein
the indication portion of the cap has
two stops separately formed on the outer end surface of the end panel;
multiple positioning holes formed on the outer end surface of the end panel and arranged in an arc between the stops; and
multiple labels formed on the outer end surface of the end panel and respectively corresponding in position to the positioning holes;
the inner tube further has
a connecting pipe mounted on the open end of the inner tube;
an adjusting portion formed on the outer surface of the sidewall of the inner tube and around the open end of the inner tube, and the adjusting portion having a lower edge; and
an indicator formed on and protruding from the adjusting portion and having
a bottom facing the indication portion of the cap; and
a positioning protrusion formed on the bottom of the indicator and selectively engaging in one of the positioning holes of the indication portion of the cap; and
the engaging groove of the inner tube is formed in and around the lower edge of the adjusting portion of the inner tube;
wherein when the positioning protrusion of the indicator of the inner tube engages in one of the positioning holes of the indication portion of the cap, one of the communicating holes of the inner tube aligns with the corresponding flow holes of the outer tube.

9. The pressure regulating oxygen bottle as claimed in claim 5, wherein
the indication portion of the cap has
two stops separately formed on the outer end surface of the end panel;
multiple positioning holes formed on the outer end surface of the end panel and arranged in an arc between the stops; and
multiple labels formed on the outer end surface of the end panel and respectively corresponding in position to the positioning holes;
the inner tube further has
a connecting pipe mounted on the open end of the inner tube;
an adjusting portion formed on the outer surface of the sidewall of the inner tube and around the open end of the inner tube, and the adjusting portion having a lower edge; and
an indicator formed on and protruding from the adjusting portion and having
a bottom facing the indication portion of the cap; and
a positioning protrusion formed on the bottom of the indicator and selectively engaging in one of the positioning holes of the indication portion of the cap; and
the engaging groove of the inner tube is formed in and around the lower edge of the adjusting portion of the inner tube;

wherein when the positioning protrusion of the indicator of the inner tube engages in one of the positioning holes of the indication portion of the cap, one of the communicating holes of the inner tube aligns with the corresponding flow holes of the outer tube.

10. The pressure regulating oxygen bottle as claimed in claim 6, wherein the indication portion of the cap has
two stops separately formed on the outer end surface of the end panel;
multiple positioning holes formed on the outer end surface of the end panel and arranged in an arc between the stops; and
multiple labels formed on the outer end surface of the end panel and respectively corresponding in position to the positioning holes;

the inner tube further has
a connecting pipe mounted on the open end of the inner tube;
an adjusting portion formed on the outer surface of the sidewall of the inner tube and around the open end of the inner tube, and the adjusting portion having a lower edge; and
an indicator formed on and protruding from the adjusting portion and having
a bottom facing the indication portion of the cap; and
a positioning protrusion formed on the bottom of the indicator and selectively engaging in one of the positioning holes of the indication portion of the cap; and the engaging groove of the inner tube is formed in and around the lower edge of the adjusting portion of the inner tube;

wherein when the positioning protrusion of the indicator of the inner tube engages in one of the positioning holes of the indication portion of the cap, one of the communicating holes of the inner tube aligns with the corresponding flow hole of the outer tube.

11. The pressure regulating oxygen bottle as claimed in claim 7, wherein the sidewall of the outer tube has an inner surface;
the outer tube further has a covering attached to the inner surface of the sidewall of the outer tube, disposed adjacent to the closed end of the outer tube, and having multiple intermediate holes, and the intermediate holes are separately formed through the covering, are linearly arranged, and respectively align with the flow holes of the outer tube; and
the inner tube is rotatably mounted in the outer tube and abuts the covering.

12. The pressure regulating oxygen bottle as claimed in claim 8, wherein the sidewall of the outer tube has an inner surface;
the outer tube further has a covering attached to the inner surface of the sidewall of the outer tube, disposed adjacent to the closed end of the outer tube, and having multiple intermediate holes, and the intermediate holes are separately formed through the covering, are linearly arranged, and respectively align with the flow holes of the outer tube; and
the inner tube is rotatably mounted in the outer tube and abuts the covering.

13. The pressure regulating oxygen bottle as claimed in claim 9, wherein the sidewall of the outer tube has an inner surface;
the outer tube further has a covering attached to the inner surface of the sidewall of the outer tube, disposed adjacent to the closed end of the outer tube, and having multiple intermediate holes, and the intermediate holes are separately formed through the covering, are linearly arranged, and respectively align with the flow holes of the outer tube; and
the inner tube is rotatably mounted in the outer tube and abuts the covering.

14. The pressure regulating oxygen bottle as claimed in claim 10, wherein the sidewall of the outer tube has an inner surface;
the outer tube further has a covering attached to the inner surface of the sidewall of the outer tube, disposed adjacent to the closed end of the outer tube, and having multiple intermediate holes, and the intermediate holes are separately formed through the covering, are linearly arranged, and respectively align with the flow holes of the outer tube; and
the inner tube is rotatably mounted in the outer tube and abuts the covering.

15. The pressure regulating oxygen bottle as claimed in claim 11, wherein a diameter of the open end of the outer tube is larger than a diameter of the closed end of the outer tube.

16. The pressure regulating oxygen bottle as claimed in claim 12, wherein a diameter of the open end of the outer tube is larger than a diameter of the closed end of the outer tube.

17. The pressure regulating oxygen bottle as claimed in claim 13, wherein a diameter of the open end of the outer tube is larger than a diameter of the closed end of the outer tube.

18. The pressure regulating oxygen bottle as claimed in claim 14, wherein a diameter of the open end of the outer tube is larger than a diameter of the closed end of the outer tube.

* * * * *